United States Patent
Rothenhaeusler (10) Patent No.: US 8,541,732 B2
(45) Date of Patent: Sep. 24, 2013

(54) OPTICAL MODULE HAVING A MULTIFOCAL OPTICAL SYSTEM WITH AN ADDITIONAL OPTICAL ELEMENT FOR COVERING A FAR RANGE AND A NEAR RANGE IN ONE IMAGE

(75) Inventor: Konrad Rothenhaeusler, Achberg (DE)

(73) Assignee: ADC Automotive Distance Control Systems GmbH, Lindau (DE)

( * ) Notice: Subject to any disclaimer, the term of this patent is extended or adjusted under 35 U.S.C. 154(b) by 265 days.

(21) Appl. No.: 13/140,957

(22) PCT Filed: Dec. 17, 2009

(86) PCT No.: PCT/DE2009/001759
§ 371 (c)(1),
(2), (4) Date: Jun. 20, 2011

(87) PCT Pub. No.: WO2010/072198
PCT Pub. Date: Jul. 1, 2010

(65) Prior Publication Data
US 2011/0253917 A1      Oct. 20, 2011

(30) Foreign Application Priority Data
Dec. 23, 2008   (DE) .......................... 10 2008 062 977

(51) Int. Cl.
*H01L 27/00* (2006.01)

(52) U.S. Cl.
USPC .................................. 250/208.1; 250/227.25

(58) Field of Classification Search
USPC ......... 250/208.1, 227.25, 216, 573; 340/602, 340/901–903; 318/DIG. 2, 444, 483; 351/206–211
See application file for complete search history.

(56) References Cited

U.S. PATENT DOCUMENTS

| | | |
|---|---|---|
| 4,515,443 A | 5/1985 | Bly |
| 4,741,605 A | 5/1988 | Alfredsson et al. |
| 6,452,148 B1 | 9/2002 | Bendicks et al. |

(Continued)

FOREIGN PATENT DOCUMENTS

| | | |
|---|---|---|
| DE | 202 07 170 | 8/2002 |
| DE | 197 00 665 | 7/2004 |

(Continued)

OTHER PUBLICATIONS

International Search Report of the International Searching Authority for International Application PCT/DE2009/001759, mailed Mar. 31, 2010, 2 pages, European Patent Office, HV Rijswijk, Netherlands.

(Continued)

*Primary Examiner* — Que T Le
(74) *Attorney, Agent, or Firm* — W. F. Fasse (57) ABSTRACT

The invention relates to an optical module having a semiconductor element (4) with a surface that is sensitive to electromagnetic radiation and with an objective lens (1) for the projection of electromagnetic radiation onto the sensitive surface of the semiconductor element (4), in particular for the use thereof in motor vehicles. An additional optical element (11) is arranged in a defined partial volume in the space between the objective lens (1) and the sensitive surface of the semiconductor element (4) so that, by the additional optical element (11), a first distance range (8) is imaged in a first region of the sensitive surface of the semiconductor element (4) and a second distance range (9) is imaged in a second region of the visual range where the additional optical element (11) is not located.

28 Claims, 2 Drawing Sheets

(56) References Cited

U.S. PATENT DOCUMENTS

| | | | |
|---|---|---|---|
| 6,617,564 B2 * | 9/2003 | Ockerse et al. | 250/208.1 |
| 7,863,568 B2 | 1/2011 | Fleury | |
| 2003/0066955 A1 | 4/2003 | Schaub et al. | |
| 2005/0063071 A1 | 3/2005 | Wang et al. | |
| 2007/0075220 A1 | 4/2007 | Kotani | |
| 2008/0265134 A1 | 10/2008 | Kinoshita | |
| 2008/0296577 A1 | 12/2008 | Yuan et al. | |
| 2009/0085755 A1 | 4/2009 | Schafer et al. | |
| 2009/0128629 A1 | 5/2009 | Egbert et al. | |
| 2012/0153154 A1 | 6/2012 | Rothenhaeusler et al. | |

FOREIGN PATENT DOCUMENTS

| | | |
|---|---|---|
| DE | 102004037871 | 3/2006 |
| DE | 102005004513 | 3/2006 |
| DE | 102006008274 | 8/2007 |
| EP | 1 580 092 | 9/2005 |
| EP | 1 764 835 | 3/2007 |
| EP | 1 923 280 | 5/2008 |
| EP | 2 062 777 | 5/2009 |
| JP | 2005-292544 | 10/2005 |
| JP | 2006-184844 | 7/2006 |
| WO | WO 99/15381 | 4/1999 |
| WO | WO 2005/075248 | 8/2005 |
| WO | WO 2006/015905 | 2/2006 |
| WO | WO 2006/121954 | 11/2006 |

OTHER PUBLICATIONS

English Translation of PCT International Preliminary Report on Patentability of the International Searching Authority for International Application PCT/DE2009/001759, mailed Jul. 21, 2011, 5 pages, International Bureau of WIPO, Geneva, Switzerland.

German Search Report for German Application No. 10 2008 062 977.4, dated Oct. 19, 2009, 4 pages, with English translation, 4 pages, Muenchen, Germany.

* cited by examiner

OPTICAL MODULE HAVING A MULTIFOCAL OPTICAL SYSTEM WITH AN ADDITIONAL OPTICAL ELEMENT FOR COVERING A FAR RANGE AND A NEAR RANGE IN ONE IMAGE

The invention relates to an optical module for covering a far range and a near range in one image. Such an optical module is particularly used in a motor vehicle for observing the region outside the motor vehicle through the windscreen.

Intelligent driver assistance systems, such as the detection of various kinds of objects in road traffic, show the flexible use of camera systems.

Modern motor vehicle sensors that are arranged on the windscreen and look through it are, e.g., the vehicle camera, the night vision camera or various optical distance sensors. These optical sensors, just like the driver of the motor vehicle, need clear vision in order to avoid any incorrect measuring signals.

Water drops, snow and dirt on the windscreen are usually removed by an electric windscreen wiper having a rubber lip. The windscreen wipers of the majority of the currently used motor vehicles are switched on and off manually. In an increasing number of cases, this task of the driver of the motor vehicle is handled by an optoelectronic rain sensor.

The operational principle of an optoelectronic rain sensor is based on the coupling of light into the windscreen at an angle that fulfils the condition of total internal reflection between glass and air but is smaller than the angle required for a total internal reflection between glass and water. When the windscreen is dry, a great part of the luminous beam coupled into the windscreen is totally reflected at the outer surface of the windscreen and decoupled at the inner surface of the windscreen at the receiver.

When there are water drops on the windscreen, the angle condition for total internal reflection is not fulfilled any more, whereby a part of the luminous beam is decoupled by the water drops and cannot reach the receiver in the passenger compartment of the vehicle any more.

This principle of rain detection is very interference-prone and dependent on the size of the drops. This principle of measurement often fails when there is drizzle since the decoupled light signal and thus the difference of the receiver signal is too low for reliable rain detection.

Thus, the optoelectronic rain sensor also has difficulty in detecting snowflakes that disintegrate and form fine droplets when they hit the windscreen. Said sensor also has problems with dry dirt and with insects that hit the windscreen.

The capacitive rain sensor is a further principle of rain detection ready to go into mass production. The sensor principle is based on the fact that the dielectric constant of water is very different from those of glass or air. Two capacitor plates conveniently attached to the inner surface of the vehicle windscreen form, together with the medium arranged therebetween, a capacitor, wherein the aim is to enable the electric lines of force to run outwardly through the air space just above the windscreen. When there is water or wet dirt in this air space, the much higher dielectric constant of the additional medium causes an increasing total capacitance of the capacitor formed thereby. The functionality of this sensor is limited, too. The distinction between fine droplets and disturbances is a problem also for this sensor, which is why the sensitivity of the sensor has to be reduced. That is why the presence of fine droplets on the windscreen causes a relatively delayed wiping signal.

A disadvantage of both sensors consists in the fact that they occupy a relatively large area on the windscreen. A reduction of the sensor area would delay the response of the sensor at the beginning of rainfall even more since the probability of one of the first drops hitting a smaller sensor field decreases.

The driver expects comfort electronics (that he or she usually obtains for an extra charge) to function fast and reliably. Ideally, the response time and the wiping behaviour of the automatic system should be the same as those of the driver of the motor vehicle in order to prevent the automatic system from being annoying or disturbing. For example, the windscreen should be already wiped when there is drizzle. A washing program is required when the amount of dirt on the windscreen caused by insects is increasing. When there are streaks on the windscreen, it should be wiped again.

In a lot of these situations, the sensors ready to go into mass production that have been developed so far fail on account of the fact that their simple sensor structures do not enable them to distinguish properly.

In the future, the necessity of avoiding a further accumulation of sensor elements of various driver assistance systems and comfort systems in the extremely limited space in the upper region of the windscreen will demand the integration of several sensors so that one single multifunctional sensor is formed.

Considering the above-mentioned facts one comes to the approach of integrating a rain sensor function as a video-based rain sensor into an existing vehicle camera that observes the region outside a motor vehicle. Imaging a far range and a near range (windscreen) onto one image sensor by means of combinations with additional optical components is a known method, wherein one approach consists in arranging a front lens in a part of the lens coverage in front of the objective lens of the vehicle camera. In this manner, the part of the beam path passing through the front lens forms a sharp image of the near range on the image sensor and the remaining part forms an image of the far range (road scene).

Patent DE 102004037871 B4 shows an appropriate optical module for an assistance system, said system covering the region outside a motor vehicle in the direction of motion of the vehicle, i.e., the region in front of the vehicle. Said patent proposes the alternating use of an image sensor for an outside-region assistance function and for a rain functionality.

With this approach, the transition region between the near range and the far range is extremely blurred, which is caused by the very unfavourable position of the lens that is arranged a short distance in front of the entrance pupil. Almost the complete image is blurred. The precise alignment of the optical means (mirror, beam splitter, near-focussing optics or front lens) for imaging the near range is difficult. Moreover, the shown solutions always require expensive additional optical means.

The object of the invention is to provide a cost-effective, stable and reliable optical system for a camera sensor.

The subject matter of the invention is an optical module having a semiconductor element with a surface that is sensitive to electromagnetic radiation and with a lens or a combination of lenses (objective lens) for the projection of electromagnetic radiation onto the sensitive surface of the semiconductor element. An additional optical element is arranged in a defined partial volume in the space between the objective lens and the sensitive surface of the semiconductor element.

By this additional, partial optical element, a first distance range, preferably the far range, is imaged onto a first region of the sensitive surface of the semiconductor element. A second distance range, preferably the near range, is imaged in the second region of the lens coverage or of the sensitive surface of the semiconductor element where the additional optical element is not located.

Therefore, the electromagnetic radiation passing through the entire width of the additional optical element is detected on the sensitive surface of the semiconductor element in a first region. The electromagnetic radiation outside the additional optical element or not passing through the entire width of said element is detected in the second region. Thus, the additional optical element takes up a part of the space in front of the sensitive surface of the semiconductor element, through which space the electromagnetic radiation reaches the sensitive surface. The additional optical element is not located in the entire object distance but in a partial field of the image distance of the objective lens.

In a subsequent image processing step, the overall image made up of the two partial images of the two different distance ranges can be evaluated in a cycle or separately.

According to a preferred embodiment of the invention, the index of refraction of the additional optical element is higher than the index of refraction of the medium surrounding the additional optical element. Typically, the medium surrounding the additional optical element is air. The image formation of the second distance range is only marginally influenced by the additional optical element and is therefore dependent on the medium surrounding the additional optical element, said medium having a lower index of refraction.

Preferably, the objective lens is positioned or adjusted in such a manner and the thickness or the index of refraction of the additional optical element is predetermined in such a manner that an optical far range is imaged in the first region of the sensitive surface of the semiconductor element and an optical near range is imaged in the second region. The near range is on the order of centimeters and the far range corresponds to the range from about two meters.

When the objective lens is positioned according to the invention, the formation of a sharp image of the near range results in the formation of a very blurred, out-of-focus image of the far range unless an additional optical element is arranged in the optical module.

The far range is imaged by the additional, partial optical element. The near field is imaged in that region of the lens coverage where this partial optical element is not located.

The bifocal or multifocal optical system of the optical module is based on the principle of the axial offset of a refractive plane face, wherein the camera is not focussed on the far range, as described in the state of the art, but focussed on an object distance of few centimeters. This object distance describes, e.g., a plane lying in the point of intersection of the lower lens coverage of the camera with the windscreen plane. In this manner, a sharply focussed image of this near field plane is created on the image sensor. For making the other driver assistance functions possible, a sharp image of the far range has to be formed on a large part of the image sensor, which is achieved by placing the partial optical element in that portion of the beam path in front of the image sensor which is to be used for imaging the far field. The thickness of the partial optical element results, in dependence on the index of refraction of the material, from the required axial offset between the image distance of the far range image and the image distance of the near range image.

According to a preferred realisation of the invention, the additional optical element is a plane-parallel transparent plate. This plane-parallel transparent plate can be particularly made of glass, e.g., of high-quality boron crown glass, borosilicate glass or the like. According to a further preferred embodiment, the plane-parallel plate can be made of a transparent synthetic material, e.g., of polycarbonate or polymethylmethacrylate (PMMA).

In a particular realisation of the invention, the entire additional optical element or only a partial volume of said element is a part of a diverging lens, is a microlens arrangement (microlens array) with diverging lenses, is an optical low-pass filter, or is a diffractive microlens array. They are preferably located on that side of the additional optical element which faces the sensitive surface of the semiconductor element. A microlens array made up of diverging lenses that widen or diverge the converging beam path in a defined manner enables the far range to be imaged at that point of the optical axis where the near field is optimally imaged.

According to an alternative embodiment, the additional optical element consists of at least two plane-parallel regions of different thicknesses, wherein the partial optical element is stepped. As an alternative, said "stepping" can be realised by a material variation within a plane-parallel transparent plate. For this purpose, materials having different indices of refraction are used in at least two regions.

Both options provide the possibility of having at least two different depth-of-field zones in one camera image, wherein said zones can overlap.

According to a further preferred embodiment, the additional optical element can be wedge-shaped so that a continuous thickness variation is achieved.

The edge of the partial optical element can preferably have a transition region that is adapted to the imaging beam path. This transition region can be stepped or wedge-shaped, for example. Disturbances caused by stray light can be avoided by blackening the transition region.

In a further development of the invention, the additional optical element can be cyclically introduced into the space between the objective lens and the image sensor, e.g., in the form of a "chopper wheel", which is a rotating disk that alternately has segments with a plane-parallel plate and segments without a plate.

In a further embodiment, a similar apparatus can be used for cyclically introducing additional optical elements having different thicknesses and/or different indices of refraction into the space between the objective lens and the image sensor, whereby images showing different depth-of-field zones in the far range can be cyclically taken. In a subsequent step, the distance of objects in the far range can be inferred from the images showing different depth-of-field zones.

According to a further embodiment, the additional optical element can be realised by filling a partial volume with a liquid medium (e.g., water or oil) having an index of refraction higher than that of the surrounding medium (typically air).

The partial optical element is preferably dimensioned in such a manner that the first region of the sensitive surface of the semiconductor element is larger than the second region. The far-image/near-image ratio is determined by the actually occupied lens coverage area by the partial optical element. We propose a ratio that ensures an image where 80% of the image show the far range and 20% of the image show the near range. Depending on the particular components and application, a 90%/10% ratio is advantageous.

Advantageously, a coating for avoiding reflections can be provided on at least one side of the additional optical element.

In addition or as an alternative, a coating for filtering electromagnetic radiation in a defined wavelength range can be provided on at least one side of the additional optical element. In particular, filter coatings for the IR and UV ranges are possible.

The region of the sensitive surface on which the near range is imaged, the beam path of which does not pass through the additional optical element, therefore receives unfiltered electromagnetic waves, i.e., also outside the visible range. For example, a UV-light filtering coating provided on the entrance side of the additional optical element can protect the element from high UV intensities, which is particularly necessary with an additional optical element made of a synthetic material.

A UV filter, either combined with the windscreen or arranged in the front region of the objective lens, can serve to filter a high UV intensity out, whereby the image sensor is protected from high UV intensities, wherein the advantage consists in the fact that the influence of the lateral colour defect is reduced since the wavelength ranges in which the objective lens is optimised are limited. Another advantage is a protective function for optical components behind the filter. Said protective function is particularly necessary with plastic lenses and for the protection of the image sensor from intense insolation.

The invention preferably provides the arrangement of the optical module in the passenger compartment of a motor vehicle behind the windscreen, wherein the optical module covers the region outside the vehicle in the direction of motion of the vehicle.

According to a preferred embodiment, the optical module is designed in such a manner that the outer surface of the windscreen, as a second distance range, is sharply imaged on the second region (near range) of the sensitive surface of the semiconductor element. By the additional optical element, the region in front of the vehicle, as a first distance range, is imaged on the first region (far range) of the sensitive surface of the semiconductor element. The semiconductor element thus covers the traffic in the far range (e.g., more than two meters) and at the same time the windscreen in the near range (e.g., less than 20 centimeters).

In a preferred further development, a camera-based rain sensor can be provided in a vehicle. The images from the first region of the sensitive surface of the semiconductor element (outer surface of the windscreen) are evaluated, wherein rain or dirt particles on the windscreen are detected. An activating output signal can be outputted to a windscreen wiper control system and/or a windscreen washer.

In a preferred realisation, an illumination source is provided that illuminates that region of the lens coverage through the windscreen which is imaged in the second region of the sensitive surface of the semiconductor element. It is advantageous to illuminate the near field with IR light. The illumination source can be advantageously controlled by means of an optical shutter, particularly with a variable illumination time of the entire sensitive surface of the semiconductor element or particularly for that part of the active surface on which the near field is imaged.

In particular, the radiation of the illumination source can be coupled into the windscreen via a flexible light guide body. A suitable flexible light guide body is, e.g., transparent silicone. The partial radiation energy can be transformed into heat by means of an absorber element attached to the windscreen. Said heat serves to heat the partial surface of the windscreen. For example, the attached heating wires of an existing windscreen heater can be used as absorber elements. At the same time, the heating wires used as an absorber surface can be used for shadowing the light radiated in the direction of motion of the motor vehicle.

A preferred embodiment provides an optical module having an additional optical element that is coated at least on one side, the wavelength filter of which suppresses that wavelength range which the illumination source uses for illuminating the near range. The region of the lens coverage through the windscreen is particularly illuminated with light in the infrared wavelength range (IR), and the additional optical element is coated with a filter that suppresses transmission in the infrared wavelength range. This wavelength range is not visible to the driver of the motor vehicle and to other road users. At the same time, the sensitive surface of the semiconductor element is highly sensitive to IR radiation so that the near field can be illuminated with IR light that has a relatively low intensity. The illumination source can be attached in several regions. Illumination can be continuous or cyclic. Cyclic illumination with a sinusoidal course of intensity or clocked illumination should be preferred in order to avoid or reduce disturbances in the image of the far range.

In addition, in an advantageous realisation, a capacitive rain sensor can be provided in the vehicle. The signals from the capacitive rain sensor and from the camera-based rain sensor are evaluated by a shared evaluation unit. Both sensor types complement one another very well, and the combination thereof provides excellent detection properties. The capacitive sensor can be advantageously realised as a strip conductor in a transparent film or in a silicone cushion, and the electronic components can be integrated into the illumination module for the camera-based rain sensor.

The camera-based rain sensor is advantageous, e.g., when there is very fine drizzle, whereas a changing capacitance under such weather conditions will hardly cause any signal change in the capacitive rain sensor. On the other hand, the capacitive rain sensor is advantageous, e.g., when there is an all-over water film on the windscreen and can reliably detect said water film on account of a substantial change in capacitance, whereas the camera-based rain sensor will find only a small number of edges in the image from which it infers the presence of raindrops.

In an advantageous realisation of the invention, a camera wedge can be arranged between the windscreen and the objective lens in the lens coverage of near-range imaging. Said camera wedge is thus arranged in the object-side beam path of near-range imaging. The camera wedge deflects electromagnetic radiation to the lens coverage of near-range imaging from a region of the windscreen through which the lens coverage of far-range imaging passes. The camera wedge can be defined by two plane faces or by one plane face and one non-planar face or by two non-planar faces. A non-planar face is a spherical, aspherical or microstructered face. In particular, the camera wedge can consist of a transparent synthetic material. The camera wedge is preferably arranged in such a manner that the thick end is at the top and the thin end is at the bottom. In this manner, the beam path of near-range imaging is deflected upwards. The camera wedge can be advantageously arranged below the beam path of far-range imaging or in the lower region thereof.

The camera wedge is preferably coated with a filter coating, wherein the filter coating suppresses particular wavelength ranges, e.g., the visible wavelength range. The upper face of the camera wedge can be advantageously blackened for the suppression of stray light.

The advantage of the use of a camera wedge is that a smaller eyehole for the camera in a blackened part of the windscreen is required and that the dimensions of the optical module or camera system are smaller.

In a preferred embodiment, a vehicle comprises an illumination source, the electromagnetic radiation of which is coupled into the windscreen via a coupling element (e.g., a flexible light guide body). A decoupling element is provided that is stuck or pressed on the windscreen so that it firmly contacts the windscreen. When there are no water drops on the windscreen, the coupled-in electromagnetic radiation is totally reflected within the windscreen. The radiation is decoupled towards the optical module by the decoupling element and imaged onto the image sensor in the region of near-range imaging (partial region for rain detection). When there are water drops on the windscreen, a part of the coupled-in electromagnetic radiation is decoupled by the water drops and not totally reflected towards the decoupling element any more. Thus, the presence of water drops and the amount of rain on the windscreen can be determined as the signal difference between the decoupled intensity in the case of a dry windscreen and the decoupled intensity in the case of a wet windscreen.

The decoupling element can be preferably coated with a special filter coating that suppresses particular wavelength ranges, e.g., the visible wavelength range.

That side of the decoupling element which faces the objective lens can be advantageously formed as a ground-glass screen by suitable surface treatment, wherein the face of the ground-glass screen is positioned in the object plane of near-range imaging.

In an extended embodiment, the decoupling element advantageously covers only a defined partial area of that partial region of the windscreen lens coverage which is covered by near-range imaging, whereby it is possible to measure the difference of the signal decoupled by the raindrops as well as to measure, in the other partial region, the signal portion scattered towards the objective lens by the drops.

The combination of both measuring methods allows a precise measurement of the wetness on the windscreen.

The invention also comprises a method for determining the distance between or of deviations of position between a windscreen and one or several optical modules. For this purpose, the optical module forms a focussed image of one or several target marks arranged on the windscreen in the second region of the sensitive surface of the semiconductor element. An evaluation unit can determine and measure a change of the position of the windscreen relative to the optical axis of the optical module compared to a stored starting position. An image processor can compute deviations of the optical axis relative to the windscreen. This method is particularly advantageous for monitoring the geometry of a stereo camera system. The change of the positions of the two stereo camera modules relative to each other can be determined from deviations of the target marks from the stored starting positions.

The invention is a particularly cost-effective solution, wherein especially the use of a simple plane-parallel glass or plastic lamina provides a cheap and very efficient solution for a multifocal optical system in an optical module.

With this optical design, the small blurred region and the simple alignment of the optical element are particularly advantageous. Compared to the installation of an optical additional element in the object distance of the camera, the installation in the image distance proposed here provides the great advantage of not having any direct coupling-in of stray light factors.

In the following, the invention will be explained on the basis of exemplary embodiments and figures.

Figure 1:
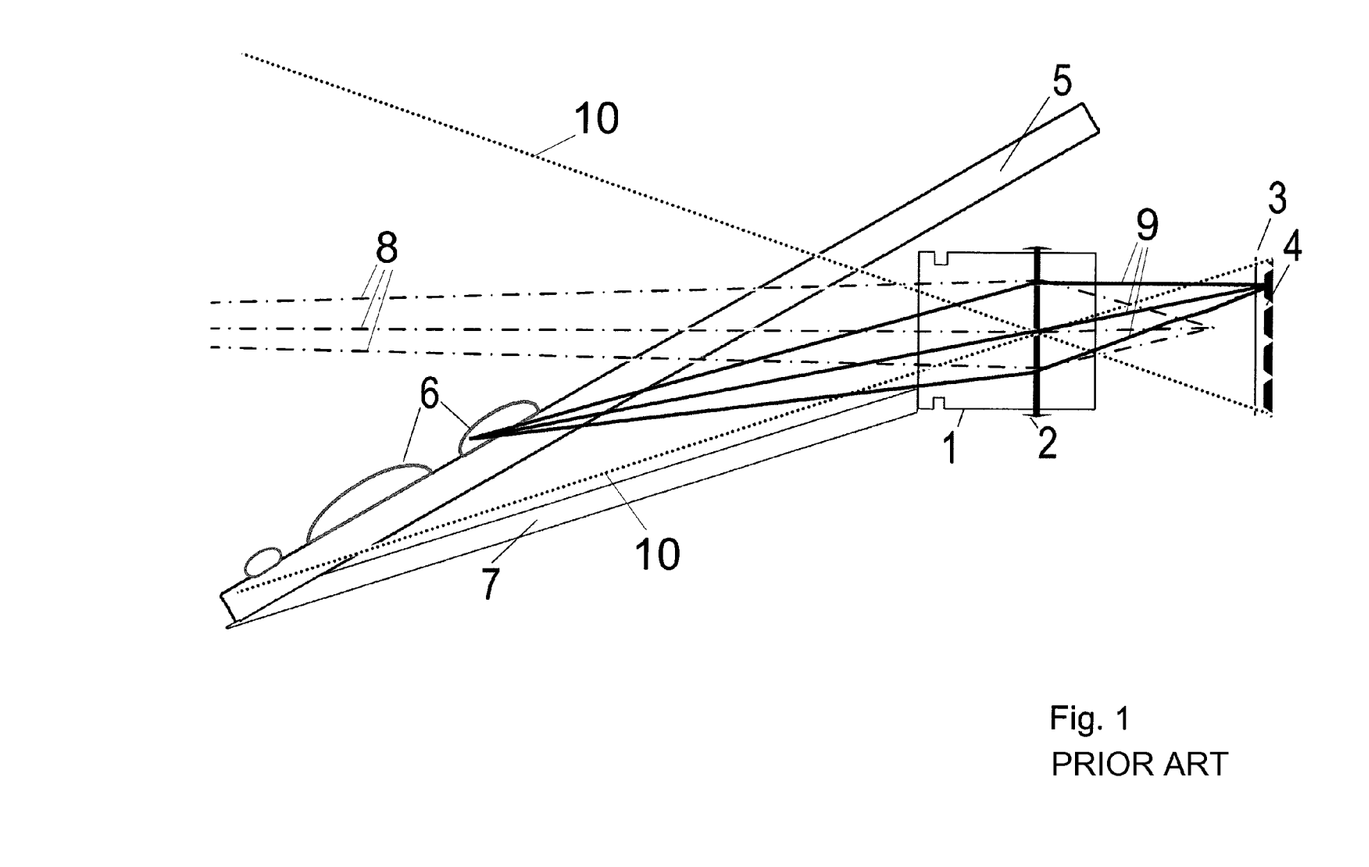
FIG. 1: Imaging properties of an optical module in a motor vehicle with an objective lens and a semiconductor sensor.

FIG. 1 shows a schematic representation of the beam paths (8, 9) for a first (8) and a second (9) distance range that are imaged onto the sensitive surface of a semiconductor element (4) by an objective lens (1) with the principal plane (2). The lens coverage (10) is demarcated by the dotted lines. The objective lens (1) is positioned between the windscreen (5) and the sensitive surface of the semiconductor element (4) in such a manner that, on the one hand, the lens coverage (10) is not restricted in its lower region by the stray light shield (7) but makes use of the available volume and, on the other hand, a focussed image of a region of the outer surface of the windscreen in the near range (9) is formed on the sensitive surface of the semiconductor element (4). If a focussed image of the far range (8) were to be formed on the sensitive surface of the semiconductor element (4), the objective lens (1) would have to be moved to the right or the semiconductor element (4) would have to be moved to the left. In both cases, the lens coverage (10) would be restricted by the stray light shield (7) and the far range would not be sharply imaged on the sensitive surface of the semiconductor element (4) any more. Such an optical module corresponds to the state of the art.

Figure 2:
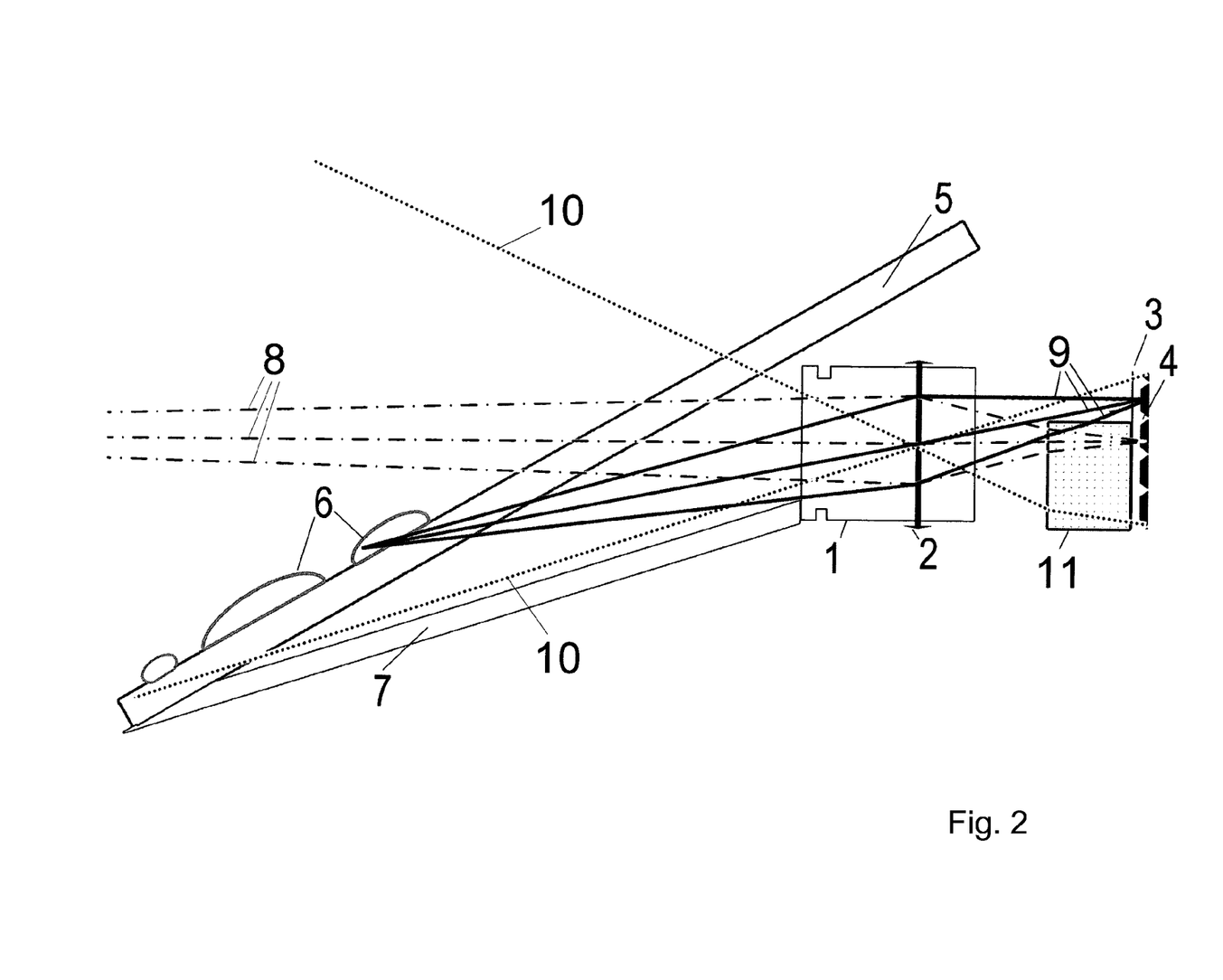
FIG. 2: Imaging properties of an optical module in a motor vehicle with an additional, partial optical element between the objective lens and the semiconductor sensor.

The parallel offset in the beam path through the windscreen (5) is not taken into consideration in the schematic representations in FIG. 1 and FIG. 2.

FIG. 2 shows an optical module with an additional optical element (11) that is arranged in a defined partial volume between the objective lens (1) and the sensitive surface of the semiconductor element (4), wherein "partial volume" relates to the fact that the additional optical element divides the visual range (10) into two parts. One part impinges on the sensitive surface of the semiconductor element (4) from the exit side (on the right) of the additional optical element (11), and the other part impinges on the sensitive surface of the semiconductor element (4) via the medium that surrounds the additional optical element (11). These two parts of the lens coverage (10) define two regions on the sensitive surface of the semiconductor element (4). The first region corresponds to that region of the semiconductor element (4) which is covered by the additional optical element (11) and in which a focussed image of the far range (8) is formed according to this representation. The second region corresponds to that region which lies above the first region and which is not covered by the additional optical element (11) and in which a focussed image of the near range (9) is formed according to this representation. In this manner, the image taken by the sensitive surface of the semiconductor element (4) contains a region with a sharp image of the near range and at the same time a region with a high-definition image of the far range. Water drops (6), dirt, snowflakes or the like can be detected and classified in the near-range image. At the same time, the traffic at a distance of, e.g., 2 to 50 meters is imaged in a large first region of the camera image and can be used and evaluated by various driver assistance functions.

A multitude of image pixels are available to a video-based rain and dirt sensor having an inventive optical module. Intelligent algorithms allow a distinction between rain, dirt, snow, ice on the windscreen or dew by means of geometric object recognition.

Edge detection algorithms, e.g., a Sobel operator, can be used in the vertical direction and/or in the horizontal direction. Edges that are exclusively detected in the vertical direction may be an indication of the presence of streaks caused by the windscreen wiper, and a signal for wiping the windscreen again or for initiating a windscreen washing process can be outputted. If streaks are persistent, the driver can be requested to change the wiper blade rubbers.

A Fourier transform, particularly FFT, can be used for frequency analysis in near-range imaging, particularly for the detection of high frequencies. A neural network can be pre-trained for the recognition of patterns from the image data by classifier with typical objects, such as raindrops of different sizes, snowflakes or dirt particles. Objects can also be recognised by means of histogram evaluation.

Image analysis can be supported and ensured by intelligent illumination, e.g., by a defined illumination function (e.g., sinusoidal course of light intensity or several illumination sources with different angles of incidence).

A further advantage of this invention is its positive influence on the present problem of temperature-dependent focus shift. The problem with an increase in temperature typically consists in the fact that the objective lens (1) moves away from the image sensor (4), whereby the focus is shifted from the far field (8) towards the near field (9). The influence of the partial optical element (11) in the image distance is evident from a refraction of the convergent beam path away from the perpendicular (transition from air to partial optical element (11) $n_{air} < n_{POE}$), whereby a sharp image of an object is formed at a greater distance from the objective lens (1) than in the case of the same design without a partial optical element (11).

When the system is heated, the distance between the image sensor (4) and the objective lens (1) is increased, as described above. At the same time, the partial optical element (11) expands and compensates for the out-of-focus image on the image sensor (4) to a certain extent. Also when temperatures are low, this combination is a positive compensator for image definition. A satisfactory image quality across the full temperature range can be achieved by optimising the material.

A camera without a partial optical element (11) is focussed on the near range. The partial optical element (11) allows the formation of a sharp image of the far range (8). A shift of the objective lens (1) away from the image sensor (4) on account of an increase in temperature is the reason for the formation of out-of-focus images of the near range (9) and the far range (8). The temperature-dependent course of near-range imaging is positive since the object distance (distance between the objective-lens principal plane (2) and the windscreen (5)) is reduced when the objective lens (1) moves away.

A further positive approach relating to temperature-dependent focus shift by the increasing image distance is the change of the lens coverage resulting therefrom, which reduces the lens coverage (10) through the windscreen (5) and thus results in the formation of images of higher object points on the same image spot. The inclined windscreen (5) does not only allow the coverage of a higher object point, but also the formation of sharp images of objects with a smaller object distance. If the focal distance does not change, a reduction of the object distance results in a larger image distance. In near-field imaging, this extension of the image distance is a self-regulating temperature compensation, wherein $1/f = 1/g + 1/b$ (f=focal distance of the objective lens; g=object distance (in the near field, e.g., 5.5 cm); b=image distance of near-field image).

This corrective process does not work with imaging in the far field (8) because, on the one hand, the object distance is much larger and changes only have a very small effect on the image distance and because, on the other hand, one does not look at an oblique plane in the object distance as in the case of the windscreen (5). For this reason, a suitable material the thermal expansion of which has a positive influence on focussing has to be chosen for the partial optical element (11).

An optimal transition region of the two image regions is ensured by a defined edge of the partial optical element (11). When elements made of glass are used, an "eroded" region of transition to the partial image of the far field (8) is caused by a glass edge where some material has chipped off. By using elements made of synthetic materials (polycarbonate or PMMA), such chipping-off on the edge can be avoided. The transition region has to be adapted to the beam path and can be wedge-shaped or stepped, for example. Moreover, the blurred region depends on the thickness of the partial optical element (11), wherein materials having high indices of refraction are advantageous.

An extended automatic windscreen-wiping and windscreen-washing and windscreen-ventilating functionality can be provided because an inventive optical module is capable of detecting different objects on the outer surface of the windscreen as well as on the inner surface of the windscreen and distinguishing between them. Rain, dirt, snow, ice, dew and aerosol deposits could be distinguished from each other on the basis of particular identifying features because of the large number of image pixels. All above-mentioned phenomena affect vision through the windscreen (5) and therefore also the other driver assistance functions that work on the basis of the data from the partial image of the far field (8).

After the steps of image processing and object detection, a control signal is outputted to the windscreen wiping system, windscreen washing system, air conditioning system or ventilating system in dependence on the detected obstacles to visibility, thereby automatically initiating a flexible cleaning function or comfort function, the kind and extent of which are adapted to the obstacle to visibility.

A further possibility of using the presented multifocal optical system is, besides the rain and dirt detection function thereof, its use as a "scanner" or code reader for a motor vehicle. A target mark on the windscreen (5) that includes, e.g., an imprinted code for windscreen identification can be read and processed. Identified codes can be transmitted to other control devices via a data line, particularly via a bus system.

We propose the use of the image of the near range (outer surface of the windscreen) as a future communication interface between man and vehicle in the form of a code reader (comparable to a recording scanner), by means of which data can be read in from outside. For example, the camera could be used for opening the vehicle, e.g., by scanning the driver's fingerprint, by moving the finger along a stored path, or by reading a presented code card.

Another example is the digital reading-in of important information that is to be communicated to the owner of a parked vehicle. The vehicle owner could view this information, e.g., on an onboard monitor.

Especially with the use of future stereo cameras, the mounting position is shifted from the middle of the windscreen to a position that is closer to the edge so that the vehicle owner can reach it more easily, wherein the camera would have to be in a stand-by phase and become active with image processing and near-range illumination when the lens coverage darkens quickly.

An alternative possibility of designing a multifocal optical system by a partial optical element (11) consists in adjusting the image distance to a best possible far-range image and using a part of a converging lens as a partial optical element (11). In this case, the near-range image without a partial optical element (11) is extremely out-of-focus. However, a converging lens (partial lens) in the image distance can collimate the imaging beam path of the near-field image, thereby allowing an image similar to that described above.

REFERENCE NUMERALS 1 objective lens
2 principal plane of objective lens
3 covering glass of semiconductor element
4 semiconductor element with sensitive surface
5 windscreen 6 raindrops
7 stray light shield
8 far range
9 near range
10 visual range
11 additional, partial optical element

The invention claimed is:

1. An optical module, comprising
a semiconductor element (4) with a sensitive surface that is sensitive to electromagnetic radiation,
an objective lens (1) adapted and arranged for the projection of electromagnetic radiation onto the sensitive surface of the semiconductor element (4), and
an additional optical element (11) arranged in a defined partial volume in a space between the objective lens (1) and the sensitive surface of the semiconductor element (4),
wherein the objective lens (1) is positioned in such a manner and the additional optical element (11) is dimensioned and arranged in such a manner so that an optical far range (8) of the visual range (10) of the optical module is imaged by the additional optical element (11) onto a first region of the sensitive surface of the semiconductor element (4) and an optical near range (9) of the visual range (10) of the optical module is imaged by the objective lens onto a second region of the sensitive surface of the semiconductor element where the additional optical element (11) is not located.

2. The optical module according to claim 1, characterized in that a first index of refraction of the additional optical element (11) is higher than a second index of refraction of a medium surrounding the additional optical element (11).

3. The optical module according to claim 1, characterized in that the additional optical element (11) is a plane-parallel transparent plate.

4. The optical module according to claim 3, characterized in that the plane-parallel transparent plate (11) is made of a synthetic plastic material.

5. The optical module according to claim 1, characterized in that the additional optical element (11) is a part of a diverging lens, is a microlens array with diverging lenses or is a diffractive microlens array.

6. The optical module according to claim 1, characterized in that the additional optical element (11) comprises at least two plane-parallel regions of different thicknesses.

7. The optical module according to claim 1, characterized in that the additional optical element (11) comprises at least two regions respectively comprising different materials having different indices of refraction.

8. The optical module according to claim 1, characterized in that the additional optical element (11) is wedge-shaped.

9. The optical module according to claim 1, adapted and arranged so that the additional optical element (11) can be cyclically introduced into the space between the objective lens (1) and the sensitive surface of the semiconductor element (4).

10. The optical module according to claim 1, characterized in that the additional optical element (11) comprises, in the partial volume, a liquid medium having a first index of refraction higher than a second index of refraction of a surrounding medium that surrounds the additional optical element.

11. The optical module according to claim 1, characterized in that the additional optical element (11) is dimensioned in such a manner so that the first region of the sensitive surface of the semiconductor element is larger than the second region.

12. The optical module according to claim 1, further comprising a coating by which reflections can be avoided, provided on at least one side of the additional optical element (11).

13. The optical module according to claim 1, further comprising a coating for filtering electromagnetic radiation in a defined wavelength range, provided on at least one side of the additional optical element (11).

14. A vehicle including an optical module according to claim 1, characterized in that the optical module is arranged in a passenger compartment of the vehicle behind a windscreen (5) of the vehicle, and the visual range of the optical module covers a region outside the vehicle in a direction of motion of the vehicle.

15. The vehicle according to claim 14, characterized in that the objective lens (1) of the optical module is positioned in such a manner so that an outer surface of the windscreen (5) is sharply imaged on the second region of the sensitive surface of the semiconductor element (4).

16. The vehicle according to claim 15, further comprising an evaluation unit in which the image from the second region of the sensitive surface of the semiconductor element (4) is evaluated, wherein rain and/or dirt particles on the windscreen (5) are detected and an output signal of the evaluation unit is outputted to a windscreen wiper control system and/or a windscreen washer control system of the vehicle.

17. The vehicle according to claim 14, further comprising an illumination source that illuminates the optical near range (9) of the visual range (10) through the windscreen (5) which is imaged in the second region of the sensitive surface of the semiconductor element (4).

18. The vehicle according to claim 17, characterized in that radiation of the illumination source is coupled into the windscreen (5) via a flexible light guide body.

19. The vehicle according to claim 17, characterized in that the illumination source illuminates the optical near range (9) of the visual range (10) through the windscreen (5) with light in an infrared wavelength range and the additional optical element (11) is coated with a filter that suppresses transmission in the infrared wavelength range.

20. The vehicle according to claim 14, wherein the optical module forms a camera-based rain sensor, and the vehicle further comprises a capacitive rain sensor and a shared evaluation unit that evaluates signals from the capacitive rain sensor and from the camera-based rain sensor.

21. The vehicle according to claim 14, further comprising a camera wedge arranged between the windscreen (5) and the objective lens (1) in an object-side beam path of the optical near range (9).

22. The vehicle according to claim 21, characterized in that the camera wedge is coated with a filter coating that suppresses particular wavelength ranges.

23. The vehicle according to claim 21, characterized in that an upper, face of the camera wedge is blackened for the suppression of stray light.

24. The vehicle according to claim 18, further comprising a decoupling element that firmly contacts the windscreen (5) and decouples the radiation coupled into the windscreen so that the radiation is imaged in the second region of the sensitive surface of the semiconductor element (4).

25. The vehicle according to claim 24, characterized in that the decoupling element is coated with a filter coating that suppresses particular wavelength ranges.

26. The vehicle according to claim 24, characterized in that a side of the decoupling element which faces the objective lens (1) has a mat surface.

27. The vehicle according to claim 24, characterized in that the decoupling element covers an area of the windscreen (5) through which the optical near range is imaged.

28. A method for calibrating a distance and a position between the windscreen (5) and the optical module in the vehicle according to claim 10, characterized in that the optical module forms, on the sensitive surface of the semiconductor element (4), a focused image of a target mark arranged on the windscreen (5) so that an evaluation unit measures a change of the position of the windscreen (5) relative to an optical axis of the optical module compared to a stored starting position.

* * * * *

UNITED STATES PATENT AND TRADEMARK OFFICE
CERTIFICATE OF CORRECTION

| | | |
|---|---|---|
| PATENT NO. | : 8,541,732 B2 | Page 1 of 1 |
| APPLICATION NO. | : 13/140957 | |
| DATED | : September 24, 2013 | |
| INVENTOR(S) | : Konrad Rothenhaeusler | |

It is certified that error appears in the above-identified patent and that said Letters Patent is hereby corrected as shown below:

In the Claims

Column 12,
Line 55, after "upper", delete ",";

Column 13,
Line 6, after "according to", "claim 10," should read --claim 14,--.

Signed and Sealed this
First Day of April, 2014

Michelle K. Lee
*Deputy Director of the United States Patent and Trademark Office*